US00PP13277P3

(12) United States Plant Patent
Olesen et al.

(10) Patent No.: US PP13,277 P3
(45) Date of Patent: Nov. 26, 2002

(54) COMPACT FLORIBUNDA ROSE PLANT NAMED 'POULAC002'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 0 days.

(21) Appl. No.: 09/780,134

(22) Filed: Feb. 8, 2001

(65) Prior Publication Data

US 2002/0152518 P1 Oct. 17, 2002

(51) Int. Cl.[7] ..... A01H 5/00

(52) U.S. Cl. ..... Plt./145

(58) Field of Search ..... Plt./145, 141

*Primary Examiner*—Bruce R. Campell
*Assistant Examiner*—June Hwu

(57) ABSTRACT

A new compact floribunda rose plant which has abundant, yellow flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

BOTANICAL CLASSIFICATION

*Rosa hybrida* 'POULac002'.

SUMMARY OF THE INVENTION

The present invention constitutes a new and distinct variety of a compact floribunda rose plant which originated from a controlled crossing between 'POULrim', described and illustrated in U.S. Plant Pat. No. 12,465 issued on Mar. 19, 2002 and 'POULjol', an unpatented variety. The two parents were crossed and the resulting seeds were planted in a controlled environment. The new variety is named 'POULac002'.

The new rose may be distinguished from its seed parent, 'POULrim', by the following combination of characteristics:

1. 'POULrim' is a hybrid tea rose and is both taller and wider in habit.

2. 'POULrim' has orange flowers.

3. 'POULrim' has greater anthocyanin intonation in stems, leaves and reproductive parts.

The new variety may be distinguished from its pollen parent, 'POULjol', created by the same inventors, by the following combination of characteristics:

1. 'POULjol's flowers are a lighter shade of yellow.

2. 'POULjol' has semi-double flowers whereas the applicants' variety has double flowers.

The objective of the hybridization of this rose variety for commercial culture was to create a new and distinct variety with unique qualities, such as:

1. Uniform and abundant large yellow flowers;

2. Vigorous and compact growth;

3. Year-round flowering under glasshouse conditions;

4. Suitability for production from softwood cuttings in pots;

5. Durable flowers and foliage which make a variety suitable for distribution in the floral industry.

This combination of qualities is not present in previously available commercial cultivars of this type and distinguish 'POULac002' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensborg, Denmark.

'POULac002' was selected by the inventors as a single plant from the progeny of the hybridization in spring 1996.

Asexual reproduction of 'POULac002' by cuttings and traditional budding was first done by L. Pernille and Mogens N. Olesen in their nursery in Fredensborg, Denmark in June 1996. This initial and other subsequent propagations conducted in controlled environments have demonstrated that the characteristics of 'POULac002' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULac002'. Specifically illustrated in SHEET 1:

FIG. 1. Stem with flower;

FIG. 2. Flower bud, partially opened bud, and open bloom;

FIG. 3. Flower petals, detached;

FIG. 4. Sepals, receptacle, and pedicel;

FIG. 5. Flowering stem as well as a bare stem exhibiting thorns;

FIG. 6. Leaves.

DETAILED DESCRIPTION OF THE VARIETY

The following is a description of 'POULac002', as observed in its growth in Burlington, Ontario, Canada, on plants aged sixteen weeks. Color references are made using The Royal Horticultural Society (London, England) Colour Chart, 1995, except where common terms of color are used.

For a comparison, several physical characteristics of the rose variety 'POULrim', a rose variety from the same inventors described and illustrated in U.S. Plant Pat. No. 12,465 issued on Mar. 19, 2000 are compared to 'POULac002' in Chart 1.

CHART 1

| | 'POULac002' | 'POULrim' |
|---|---|---|
| Size of open bloom | 45–55 mm | 100–120 mm |
| Open flower; color of upper surface | Yellow-Orange Group 15A | Blend of Orange Group 29B–29C |
| Petalage | Double, 20–28 | Double, 25–30 |

Classification:

*Commercial.*—Compact floribunda.

Parents: 'POULrim'×'POULjol'.

FLOWER AND FLOWER BUD

Blooming habit: Continuous.

Flower bud:

*Size.*—Upon opening, 24–27 mm in length from base of receptacle to end of bud.

*Bud form.*—Short and globular.

*Bud color.*—As sepals unfold, Orange-Red Group 31B. Guard petals have variable coloration of Yellow-Green Group 146C and Red Group 50A. Yellow-Orange Group 21B at ¼ opening.

*Sepals.*—Yellow-Green Group 147A. Moderate foliaceous appendages on 3 of the 5 sepals. Surfaces of sepals slightly pubescent. Stipitate glands are present on margin of sepals with a limited number of stipitate glands on lower surface of sepal. Sepal size is 25 mm (l)×11 mm (w).

*Receptacle.*—Surface: Smooth. Shape: Urn-shaped. Size: Medium. 8 mm(h)×10 mm (w). Color: Green Group 143C.

*Peduncle.*—Surface: Smooth near receptacle with stipitate glands on lower portion. Length: 30 to 38 mm average length. Color: Yellow-Green Group 144A. Strength: Erect.

*Borne.*—Singularly. One bud per flowering stem.

Flower bloom:

*Fragrance.*—Light fruity scent.

*Duration.*—As a pot plant, flowers last from 15 to 18 days. As a cut flower 4 to 5 days. The blooms have a duration on the plant of approximately 8 to 12 days.

*Size.*—Large for an 12–15 cm pot rose. Average flower diameter is 45–55 mm when open.

*Form.*—Shape of flower when viewed from the side: Upon opening, upper part: Flat. Upon opening, lower part: Flat. Open flower, upper part: Flattened convex. Open flower, lower part: Flattened convex.

*Petalage.*—Double. Average range: 20–28 petals under normal conditions with 1–3 petaloids.

Color:

*Upon opening, petals.*—Outermost petals: Outer Side: Yellow-Orange Group 15A. Inner Side: Yellow-Orange Group 15B. Often exhibiting intonations of Green Group 141C in middle zone of petal. Innermost petals: Outer Side: Yellow-Orange Group 14A. Inner Side: Yellow-Orange Group 14B–C.

*Upon opening basal petal spots.*—No distinctive coloration at petal base observed.

*After opening, petals.*—Outermost petals: Outer Side: A blend of Yellow Group 14B to Orange Group 28B. Inner Side: A blend of Orange-Red Group 32B and Yellow-Orange Group 21C. Innermost petals: Outer Side: Yellow-Orange Group 14A. Inner Side: Yellow-Orange Group 15B with Orange-Red Group 33C intonation in basal zone.

*After opening, basal petal spots.*—No distinctive coloration at petal base observed.

General tonality: On open flower, Yellow Group 13B. No change in the general tonality at the end of the 4$^{th}$ day. Afterwards, general tonality is Yellow-Orange Group 14C.

Petals:

*Size.*—30–35mm (l)×25–35 mm (w).

*Petal reflex.*—Slightly.

*Petal edge.*—Slightly ruffled.

*Shape.*—Deltoid; apex is rounded and base is acute.

*Petaloids.*—Quantity: 1–3. Color: Upper surface is Yellow Group 13B. Lower surface is Yellow Group 13B. Size: 10 mm (l)×7 to 10 mm (w). Texture: Smooth.

*Thickness.*—Thick.

*Arrangement.*—Informal.

Reproductive organs:

*Pollen.*—Color: Yellow-Orange Group 17A. Quantity: Very abundant.

*Anthers.*—Size: 3 mm long. Color: Yellow Group 11A. Quantity: 25 to 30.

*Filaments.*—Color: Yellow-Orange Group 17A. Length: 10 mm.

*Stigmas.*—Inferior in location to anthers. Color: Greyed-Orange Group 163C with intonations of Red Group 43D at base of stigma. Length: 1 mm.

*Styles.*—Color: Yellow-Green Group 153C. Length: 7 mm. Quantity: 20 to 25.

*Hip formation.*—Not observed.

PLANT

Plant growth: Vigorous, and compact. When grown as a 15-cm pot plant, the average height of the plant is 22–25 cm and the average width is 26–30 cm. Field grown plants were not observed.

Stems:

*Color.*—Young wood: Yellow-Green Group 146B. Older wood: Yellow-Green Group 146C.

*Prickles.*—Incidence: Few. Size: Average length: 3–4 mm. Color: Greyed-Red Group 181B. Shape: Concave to deeply concave.

*Surface.*—Young wood: Smooth. Older wood: Smooth.

*Anthocyanin.*—Not observed on stems.

Plant foliage: Typical number of leaflets on normal leaves in middle of the stem: 5 leaflets.

Typical leaf size: Medium 110 mm (l)×120 mm (w).

*Quantity.*—Very abundant.

*Color.*—Mature Foliage: Upper Leaf Surface: Yellow-Green Group 147A. Lower Leaf Surface: Yellow-Green Group 145B. Juvenile foliage: Upper leaf surface: Yellow-Green Group 144B. Lower leaf surface: Yellow-Green Group 145B. Anthocyanin: Intonations of Greyed-Red Group 181C on lower surface of both mature and juvenile foliage. Intonations also present on upper surface of juvenile foliage.

Plant leaves and leaflets:

*Stipules.*—Size: 8–10 mm (l)×2–4 mm (w). Color: Yellow-Green Group 144A–B. Stipitate glands: Located along margins. Anthocyanin: None.

*Petiole.*—Length: 20–28 mm. Color: Yellow-Green Group 144A. Underneath: Typically one small prickle and a limited number of stipitate glands. Margins: Stipitate glands present. Anthocyanin: Not present on juvenile foliage. Intonations along margins on mature foliage. Color: Greyed-Red Group 181A.

*Rachis.*—Color: Yellow-Green Group 144B. Underneath: Few prickles Margins: Stipitate glands present. Anthocyanin: On upper surface along margins of juvenile and mature foliage. Color: Greyed-Red Group 181A.

*Leaflet.*—Edge: Serrated. Shape: Ovate; apex is cirrose and base is rounded. Other: Glossy and thick.

Disease resistance: Above average resistance to mildew, black spot, and Botrytis under normal growing conditions in Burlington, Canada.

Cold hardiness: The variety 'POULac003' has been found to be cold hardy in Fredensborg, Denmark; and Hannover, Germany.

We claim:

1. A new and distinct variety of rose plant of the compact floridbunda class, substantially as herein illustrated and described as a distinct and novel rose variety due to its abundant, yellow flowers, vigorous growth, compact habit, suitability for production from softwood cuttings in pots, and durable flowers and foliage which make the variety suitable for distribution in the floral industry.

* * * * *

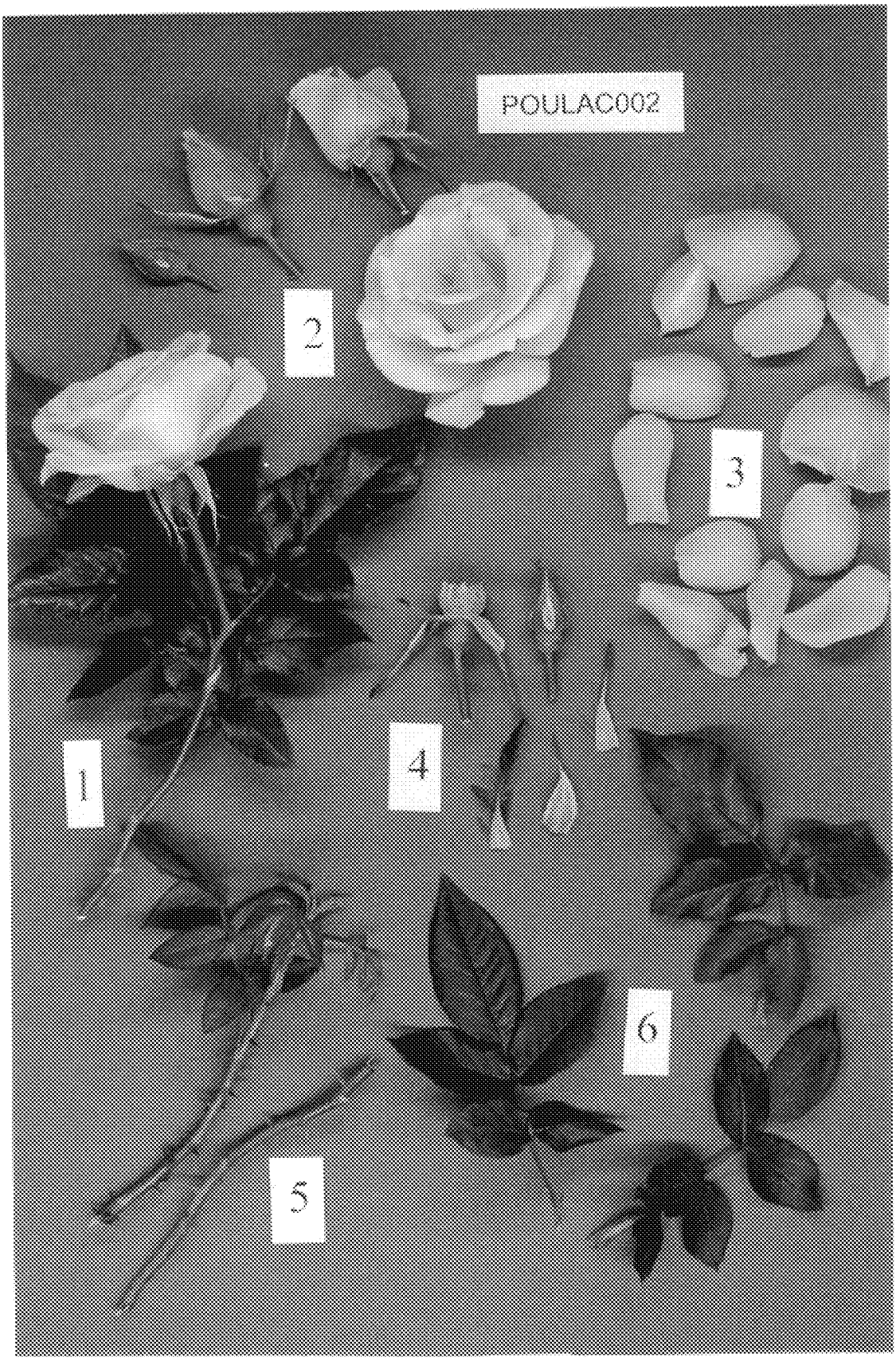
POULAC002
1
2
3
4
5
6